(12) United States Patent
Diaz-Fernández

(10) Patent No.: US 7,960,568 B2
(45) Date of Patent: Jun. 14, 2011

(54) HETEROCYCLYL-SUBSTITUTED SULFONAMIDES FOR THE TREATMENT OF COGNITIVE OR FOOD INGESTION RELATED DISORDERS

(75) Inventor: José-Luis Diaz-Fernández, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 12/525,411

(22) PCT Filed: Jan. 30, 2008

(86) PCT No.: PCT/EP2008/000726
§ 371 (c)(1),
(2), (4) Date: Sep. 21, 2009

(87) PCT Pub. No.: WO2008/092665
PCT Pub. Date: Aug. 7, 2008

(65) Prior Publication Data
US 2010/0076036 A1    Mar. 25, 2010

(30) Foreign Application Priority Data
Jan. 31, 2007   (EP) .................................. 07384014

(51) Int. Cl.
C07D 209/04 (2006.01)
C07D 513/04 (2006.01)
C07D 209/00 (2006.01)
A61K 31/40 (2006.01)
A61K 31/405 (2006.01)
A61K 31/425 (2006.01)

(52) U.S. Cl. ........ 548/491; 548/155; 548/483; 514/414; 514/415; 514/368

(58) Field of Classification Search .................. None
See application file for complete search history.

(56) References Cited

U.S. PATENT DOCUMENTS

| 5,942,536 | A * | 8/1999 | Fritz et al. ............ 514/414 |
| 7,462,640 | B2 * | 12/2008 | Merce Vidal et al. ......... 514/415 |
| 2003/0191124 | A1 * | 10/2003 | Merce-Vidal et al. ..... 514/232.8 |
| 2005/0065202 | A1 * | 3/2005 | Vidal et al. .................... 514/414 |
| 2009/0264457 | A1 * | 10/2009 | Codony-Soler et al. ...... 514/292 |
| 2010/0120886 | A1 * | 5/2010 | Diaz-Fernandez .......... 514/415 |

FOREIGN PATENT DOCUMENTS

| EP | 1445252 A1 | 8/2004 |
| EP | 1632491 A1 * | 3/2006 |
| WO | WO 9928297 A1 * | 6/1999 |
| WO | WO03042175 A2 * | 5/2003 |
| WO | WO 2004098588 A1 * | 11/2004 |
| WO | 2005014000 A | 2/2005 |
| WO | 2005014045 A | 2/2005 |
| WO | WO 2007147883 A1 * | 12/2007 |

OTHER PUBLICATIONS

Romero et al, J. Pharmacological and Toxicological Methods, 55 (2007) 144-150.*
Holenz et al., J. Med. Chem. (2005), 48 (6), 1781-1795.*
International Search Report for PCT/EP2008/000726 dated Jun. 19, 2008.

* cited by examiner

Primary Examiner — Kamal Saeed
Assistant Examiner — Nyeemah Grazier
(74) Attorney, Agent, or Firm — Heslin Rothenberg Farley & Mesiti P.C.

(57) ABSTRACT

The present invention relates to heterocyclyl-substituted sulfonamides with 5-$HT_6$ receptor affinity, and compositions thereof, and the use of said compounds for the treatment or prophylaxis of various disorders.

23 Claims, No Drawings

HETEROCYCLYL-SUBSTITUTED SULFONAMIDES FOR THE TREATMENT OF COGNITIVE OR FOOD INGESTION RELATED DISORDERS

CROSS REFERENCE TO RELATED APPLICATIONS

This application is a U.S. National Phase filing under 35 U.S.C. §371 of International Application PCT/EP2008/000726, filed Jan. 30, 2008, and published as WO 2008/092665 on Aug. 7, 2008. PCT/EP2008/000726 claimed benefit of priority from European Patent Application No. EP 07384014.2, filed Jan. 31, 2007. The entire contents of each of the prior applications are incorporated herein by reference.

The present invention relates to heterocyclyl-substituted sulfonamide compounds with 5-$HT_6$ receptor affinity, a medicament comprising a said compound, and the use of said compound for the manufacture of a medicament.

The superfamily of serotonin receptors (5-HT) includes 7 classes (5-$HT_1$-5-$HT_7$) encompassing 14 human subclasses [D. Hoyer, et al., Neuropharmacology, 1997, 36, 419]. The 5-$HT_6$ receptor is a serotonin receptor identified by molecular cloning both in rats [F. J. Monsma, et al., Mol. Pharmacol., 1993, 43, 320; M. Ruat, et al., Biochem. Biophys. Res. Commun., 1993, 193, 268] and in humans [R. Kohen, et al., J. Neurochem., 1996, 66, 47]. Compounds with 5-$HT_6$ receptor antagonistic activity are useful for the treatment of various disorders of the Central Nervous System and of the gastrointestinal tract, such as irritable intestine syndrome. Compounds with 5-$HT_6$ receptor antagonistic activity are useful in the treatment of anxiety, depression and cognitive memory disorders [M. Yoshioka, et al., Ann. NY Acad. Sci., 1998, 861, 244; A. Bourson, et al., Br. J. Pharmacol., 1998, 125, 1562; D. C. Rogers, et al., Br. J. Pharmacol. Suppl., 1999, 127, 22P; A. Bourson, et al., J. Pharmacol. Exp. Ther., 1995, 274, 173; A. J. Sleight, et al., Behav. Brain Res., 1996, 73, 245; T. A. Branchek, et al., Annu. Rev. Pharmacol. Toxicol., 2000, 40, 319; C. Routledge, et al., Br. J. Pharmacol., 2000, 130, 1606]. It has been shown that typical and atypical antipsychotic drugs for treating schizophrenia have a high affinity for 5-$HT_6$ receptors [B. L. Roth, et al., J. Pharmacol. Exp. Ther., 1994, 268, 1403; C. E. Glatt, et al., Mol. Med., 1995, 1, 398; F. J. Mosma, et al., Mol. Pharmacol., 1993, 43, 320; T. Shinkai, et al., Am. J. Med. Genet., 1999, 88, 120]. Compounds with 5-$HT_6$ receptor antagonistic activity are useful for treating infant hyperkinesia (ADHD, attention deficit/hyperactivity disorder) [W. D. Hirst, et al., Br. J. Pharmacol., 2000, 130, 1597; C. Gerard, et al., Brain Research, 1997, 746, 207; M. R. Pranzatelli, Drugs of Today, 1997, 33, 379].

Cognitive and/or degenerative brain disorders are characterized clinically by progressive loss of memory, cognition, reasoning, judgement and emotional stability that gradually leads to profound mental deterioration and ultimately death. A very important aspect of such disorders are cognitive memory disorders which in consequence tend to substantially lower the quality of life of many persons being struck by these disorders or symptoms. In another example of such disorders, Alzheimer's disease is a common cause of progressive mental failure (dementia) in aged humans and is believed to represent the fourth most common medical cause of death in the United States. In particular, Alzheimer's disease is associated with degeneration of cholinergic neurons in the basal forebrain that play a fundamental role in cognitive functions, including memory. Cognitive and/or degenerative brain disorders have been observed in varied races and ethnic groups world-wide and presents a major public health problem. These diseases are currently estimated to affect about two to three million individuals in the United States alone and the occurrence will increase world-wide as the human life span increases.

It was therefore an object of the present invention to provide a compound/medicament suitable for the prophylaxis and/or treatment of disorders related to 5-$HT_6$ receptors, which preferably does not show the undesired side effects of the conventional compounds used, or at least less frequent and/or less pronounced.

In particular, it was an object of the present invention to provide a medicament suitable for the prophylaxis and/or treatment of cognitive disorders or obesity/food ingestion disorders, which preferably does not show the undesired side effects of the conventional medicaments, or at least less frequent and/or less pronounced.

It has been found that the compounds of general formula (I) given below show affinity for the 5-$HT_6$-receptor. These compounds are therefore also suitable for the manufacture of a medicament for the prophylaxis and/or treatment of cognitive disorders or the treatment of food ingestion (food intake) disorders, particularly for the regulation of appetite, for the maintenance, increase or reduction of body weight, for the prophylaxis and/or treatment of obesity, bulimia, anorexia, cachexia or type II diabetes (Non-Insulin Dependent Diabetes Mellitus), preferably type II diabetes, which is caused by obesity.

Compounds showing similarities to the compounds according to the invention are being found in EP 1 445 252 A1, describing also compounds binding to the 5$HT_6$-receptor.

U.S. Pat. No. 3,472,870 also describes compounds in the same general chemical class as the compounds according to the invention, even though no binding to the 5$HT_6$-receptor is mentioned.

Said object above has been achieved by providing as an active substance a heterocyclyl-substituted sulfonamide compound according to general formula (I)

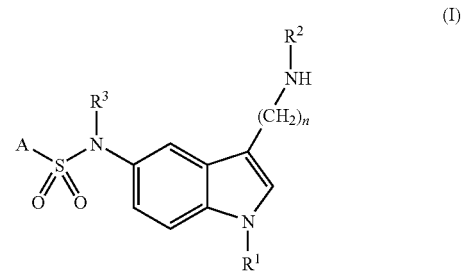

(I)

wherein
A represents an optionally at least mono-substituted mono or bicyclic heterocyclic ringsystem with 1 to 3 heteroatoms selected from oxygen, nitrogen and sulphur;
$R^1$ represents hydrogen, or $C_1$-$C_4$ alkyl or a benzyl radical;
$R^2$ represents hydrogen, or $C_1$-$C_4$ alkyl;
$R^3$ represents hydrogen or $C_1$-$C_4$ alkyl;
n represents 0, 1, 2, 3 or 4;
optionally in form of one of its stereoisomers, preferably enantiomers or diastereomers, its racemate or in form of a mixture of at least two of its stereoisomers, preferably enantiomers or diastereomers, in any mixing ratio, or a salt, preferably a physiologically acceptable salt thereof, or a corresponding solvate, respectively.

In another definition and embodiment of this invention said object above has been achieved by providing as an active substance a heterocyclyl-substituted sulfonamide compound according to general formula (I)

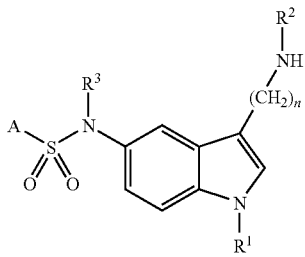

wherein
A represents an optionally at least mono-substituted mono or bicyclic heterocyclic ringsystem with 1 to 3 heteroatoms selected from oxygen, nitrogen and sulphur;
$R^1$ represents hydrogen, or a substituted or unsubstituted $C_1$-$C_4$ alkyl or a benzyl radical;
$R^2$ represents hydrogen, or a substituted or unsubstituted $C_1$-$C_4$ alkyl;
$R^3$ represents hydrogen or a substituted or unsubstituted $C_1$-$C_4$ alkyl;
n represents 0, 1, 2, 3 or 4;
optionally in form of one of its stereoisomers, preferably enantiomers or diastereomers, its racemate or in form of a mixture of at least two of its stereoisomers, preferably enantiomers or diastereomers, in any mixing ratio, or a salt, preferably a physiologically acceptable salt thereof, or a corresponding solvate, respectively.

In another definition and embodiment of this invention this was achieved by providing as an active substance a heterocyclyl-substituted sulfonamide compound according to general formula (I)

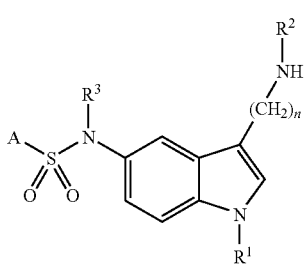

wherein
A represents an optionally at least mono-substituted mono or bicyclic heterocyclic ringsystem with 1 to 3 heteroatoms selected from oxygen, nitrogen and sulphur;
$R^1$ represents hydrogen, or an unsubstituted $C_1$-$C_4$ alkyl or a benzyl radical;
$R^2$ represents hydrogen, or an unsubstituted $C_1$-$C_4$ alkyl;
$R^3$ represents hydrogen or an unsubstituted $C_1$-$C_4$ alkyl;
n represents 0, 1, 2, 3 or 4;
optionally in form of one of its stereoisomers, preferably enantiomers or diastereomers, its racemate or in form of a mixture of at least two of its stereoisomers, preferably enantiomers or diastereomers, in any mixing ratio, or a salt, preferably a physiologically acceptable salt thereof, or a corresponding solvate, respectively.

An "aryl", "aryl radical" or group is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or monosubstituted or polysubstituted.

A "heterocyclyl", a "heterocyclyl radical" or group or "heterocyclic ring system" is understood as meaning heterocyclic ring systems which contain one or more heteroatoms from the group consisting of nitrogen, oxygen and/or sulfur in the ring or ringsystem, and can also be mono- or polysubstituted. The ringsystem may consist either of only one saturated or unsaturated or even aromatic ring or may consist of 2, 3 or 4 saturated or unsaturated or even aromatic rings, which are condensed in that between two or more of the rings ring members are shared. Examples which may be mentioned from the group of heterocyclyls are furan, benzofuran, thiophene, benzothiophene, pyrrole, pyridine, pyrimidine, pyrazine, quinoline, isoquinoline, phthalazine, benzo-1,2,5-thiadiazole, imidazo-thiazole, benzothiazole, indole, benzotriazole, benzodioxolane, benzodioxane, carbazole and quinazoline.

In connection with heterocyclyls, heterocyclyl groups or heterocyclyl radicals, "substituted" is understood—unless defined otherwise—as meaning replacement of at least one hydrogen radical on the ring-system of the heterocyclyl radical by OH, SH, =O, halogen (F, Cl, Br, I), CN, $NO_2$, COOH; $NR_xR_y$, with $R_x$ and $R_y$ independently being either H or a saturated or unsaturated, linear or branched, substituted or unsubstituted $C_{1-6}$-alkyl; by a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted S—$C_{1-6}$-alkyl; a saturated or unsaturated, linear or branched, substituted or unsubstituted —C(O)—$C_{1-6}$-alkyl; a saturated or unsaturated, linear or branched, substituted or unsubstituted —C(O)—O—$C_{1-6}$-alkyl; a substituted or unsubstituted phenyl. Within that "monosubstituted" means the substitution of exactly one hydrogen radical, whereas "polysubstituted" means the substitution of more than one hydrogen radical with "polysubstituted" radicals being understood as meaning that the replacement takes effect both on different and on the same atoms several times with the same or different substituents. Therefore, "optionally at least monosubstituted" means either "not substituted" if the option is not fulfilled, "monosubstituted" or "polysubstituted".

In the context of this invention "alkyl", "alkyl radical" or group is understood as meaning linear or branched hydrocarbons. If not expressly defined otherwise they are unsubstituted. So, if defined as "substituted or unsubstituted"—the alkyl can be unsubstituted or substituted (mono- or polysubstituted). If not expressly defined otherwise they are saturated. On the other hand unsaturated alkyl is understood to encompass alkenyl and alkinyl groups, like e.g. —CH=CH—$CH_3$ or —C≡C—$CH_3$, while saturated alkyl encompasses e.g. —$CH_3$ and —$CH_2$—$CH_3$. In these radicals, $C_{1-2}$-alkyl represents $C_1$- or $C_2$-alkyl, $C_{1-3}$-alkyl represents $C_1$-, $C_2$- or $C_3$-alkyl, $C_{1-4}$-alkyl ($C_1$-$C_4$-alkyl) represents $C_1$-, $C_2$-, $C_3$- or $C_4$-alkyl, $C_{1-5}$-alkyl represents $C_1$-, $C_2$-, $C_3$-, $C_4$-, or $C_5$-alkyl, $C_{1-6}$-alkyl represents $C_1$-, $C_2$-, $C_3$-, $C_4$-, $C_5$- or $C_6$-alkyl, $C_{1-7}$-alkyl represents $C_1$-, $C_2$-, $C_3$-, $C_4$-, $C_5$, $C_6$- or $C_7$-alkyl, $C_{1-8}$-alkyl represents $C_1$-, $C_2$-, $C_3$-, $C_4$-, $C_5$-, $C_6$-, $C_7$- or $C_8$alkyl, $C_{1-10}$-alkyl represents $C_1$-, $C_2$-, $C_3$-, $C_4$-, $C_5$-, $C_6$, $C_7$-, $C_8$-, $C_9$- or $C_{10}$-alkyl and $C_{1-18}$-alkyl represents $C_1$-, $C_2$-, $C_3$-, $C_4$-, $C_5$-, $C_6$, $C_7$-, $C_8$, $C_9$-, $C_{10}$-, $C_{11}$-, $C_{12}$-, $C_{13}$-, $C_{14}$-, $C_{15}$-, $C_{16}$-, $C_{17}$- or $C_{18}$-alkyl. The alkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc.

The term "alkylene" is understood as meaning a divalent alkyl group like $—CH_2—$ or $—CH_2—CH_2—$ with $(CH_2)_{3-6}$ being understood as meaning $—CH_2—CH_2—CH_2—$, $—CH_2—CH_2—CH_2—CH_2—$, $—CH_2—CH_2—CH_2—CH_2—CH_2—$ and $—CH_2—CH_2—CH_2—CH_2—CH_2—CH_2—$, $(CH_2)_{1-4}$ is to be understood as meaning $—CH_2—$, $—CH_2—CH_2—$, $—CH_2—CH_2—CH_2—$ and $—CH_2—CH_2—CH_2—CH_2—$, $(CH_2)_{4-5}$ is to be understood as meaning $—CH_2—CH_2—CH_2—CH_2—$ and $—CH_2—CH_2—CH_2—CH_2—CH_2—$, etc. "Alkylene" might also include a non-saturated divalent alkyl-chain.

In connection with "alkylene", "alkyl", "alkyl radical" or group—unless defined otherwise—the term "substituted" in the context of this invention is understood as meaning replacement of at least one hydrogen radical by F, Cl, Br, I, $NH_2$, SH or OH. "Substituted" includes in its definition "monosubstituted" or polysubstituted"; within that "monosubstituted" means the substitution of exactly one hydrogen radical, whereas "polysubstituted" means the substitution of more than one hydrogen radical with "polysubstituted" radicals being understood as meaning that the replacement takes effect both on different and on the same atoms several times with the same or different substituents, for example three times on the same C atom, as in the case of $CF_3$, or at different places, as in the case of e.g. $—CH(OH)—CH=CH—CHCl_2$. Therefore, "optionally at least monosubstituted" means either "not substituted" if the option is not fulfilled, "monosubstituted" or "polysubstituted". "Unsubstituted" means no substitution of any hydrogen on the alkyl or alkyl radical.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with NH4, but in particular (mono)- or (di)sodium, (mono)- or (di)potassium, magnesium or calcium salts.

These physiologically acceptable salts can also be formed with anions or acids in the context of this invention is understood as meaning salts of at least one of the compounds used according to the invention—usually protonated, for example on the nitrogen—as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be in crystalline form or either as free compounds or as solvates and it is intended that those forms are within the scope of the present invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent) especially including hydrates and alcoholates, e.g. methanolate.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or $^{15}N$-enriched nitrogen are within the scope of this invention.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I) or, or of its salts, solvates or prodrugs.

Particularly preferred is a heterocyclyl-substituted sulfonamide according to the invention according to formula (I), wherein
A represents
an optionally at least mono-substituted monocyclic heterocyclic ringsystem of 5 to 6 ring members containing 1 to 3 heteroatoms selected from oxygen, nitrogen and sulphur as ring members; or an optionally at least mono-substituted bicyclic heterocyclic ringsystem of 8 to 10 ring members containing 1 to 3 heteroatoms selected from oxygen, nitrogen and sulphur as ring members;
preferably
an optionally at least mono-substituted monocyclic heterocyclic ringsystem of 5 to 6 ring members containing 1 to 3 heteroatoms selected from oxygen, nitrogen and sulphur as ring members, wherein the heterocyclic ringsystem is unsaturated or aromatic; or an optionally at least mono-substituted bicyclic heterocyclic ringsystem of 8 to 10 ring members containing 1 to 3 heteroatoms selected from oxygen, nitrogen and sulphur as ring members; wherein at least one ring in the heterocyclic ringsystem is unsaturated or aromatic;

more preferably an unsaturated or aromatic monocyclic heterocyclic ringsystem of 5 to 6 ring members containing 1 to 3 heteroatoms selected from oxygen, nitrogen and sulphur as ring members; optionally substituted by 1 or 2 radicals R or R' selected from halogen, $C_1$-$C_4$ alkyl, O—$C_1$-$C_4$ alkyl, CN, $NO_2$, $CF_3$, $CHF_2$, $OCF_3$, OH, SH, $NH_2$, phenyl, optionally at least monosubstituted by halogen, $C_1$-$C_4$ alkyl, O—$C_1$-$C_4$ alkyl, OH, SH, $NH_2$, or a monocyclic heterocyclic ring system with 5 or 6 ring members containing 1 or 2 atoms of oxygen, nitrogen or sulphur as ring member, at least monosubstituted by halogen, $C_1$-$C_4$ alkyl, O—$C_1$-$C_4$ alkyl, OH, SH, $NH_2$;

or an unsaturated or aromatic bicyclic heterocyclic ringsystem of 8 to 10 ring members containing 1 to 3 heteroatoms selected from oxygen, nitrogen and sulphur as ring members; optionally substituted by 1 or 2 radicals R or R' selected from halogen, $C_1$-$C_4$ alkyl, O—$C_1$-$C_4$ alkyl, CN, $NO_2$, $CF_3$, $CHF_2$, $OCF_3$, OH, SH, $NH_2$; phenyl, optionally at least monosubstituted by halogen, $C_1$-$C_4$ alkyl, O—$C_1$-$C_4$ alkyl, OH, SH, $NH_2$; or a monocyclic heterocyclic ring system with 5 or 6 ring members containing 1 or 2 atoms of oxygen, nitrogen or sulphur as ring member, at least monosubstituted by halogen, $C_1$-$C_4$ alkyl, O—$C_1$-$C_4$ alkyl, OH, SH, most preferably an unsaturated or aromatic monocyclic heterocyclic ringsystem of 5 to 6 ring members containing 1 to 3 heteroatoms selected from oxygen, nitrogen and sulphur as ring members; optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, or $NH_2$;

or an unsaturated or aromatic bicyclic heterocyclic ringsystem of 8 to 10 ring members containing 1 to 3 heteroatoms selected from oxygen, nitrogen and sulphur as ring members; optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, or $NH_2$.

Also preferred is a heterocyclyl-substituted sulfonamide according to the invention according to formula (I), wherein $R^1$ represents hydrogen, $CH_3$, $C_2H_5$, $C_3H_7$ or $C_4H_9$; preferably hydrogen, methyl, ethyl, n-propyl, i-propyl, n-butyl, i-butyl and t-butyl; more preferably hydrogen, methyl or ethyl; most preferably hydrogen.

Also preferred is a heterocyclyl-substituted sulfonamide according to the invention according to formula (I), wherein $R^2$ represents hydrogen, $CH_3$, $C_2H_5$, $C_3H_7$ or $C_4H_9$; preferably hydrogen, methyl, ethyl, n-propyl, i-propyl, n-butyl, i-butyl and t-butyl; more preferably hydrogen, methyl or ethyl.

Also preferred is a heterocyclyl-substituted sulfonamide according to the invention according to formula (I), wherein $R^3$ represents hydrogen, $CH_3$, $C_2H_5$, $C_3H_7$ or $C_4H_9$; preferably hydrogen, methyl, ethyl, n-propyl, i-propyl, n-butyl, i-butyl and t-butyl; more preferably hydrogen, methyl or ethyl; most preferably hydrogen.

Also preferred is a heterocyclyl-substituted sulfonamide according to the invention according to formula (I), wherein n represents 0, 1 or 2, preferably 2.

Particularly preferred is a heterocyclyl-substituted sulfonamide according to the invention according to formula (II), wherein
A represents
an unsaturated or aromatic monocyclic heterocyclic ringsystem of 5 to 6 ring members containing 1 to 3 heteroatoms selected from oxygen, nitrogen and sulphur as ring members; optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, or $NH_2$;

or an unsaturated or aromatic bicyclic heterocyclic ringsystem of 8 to 10 ring members containing 1 to 3 heteroatoms selected from oxygen, nitrogen and sulphur as ring members; optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, or $NH_2$;
wherein
$R^2$ represents hydrogen, $CH_3$, $C_2H_5$, $C_3H_7$ or $C_4H_9$;

optionally in form of one of its stereoisomers, preferably enantiomers or diastereomers, its racemate or in form of a mixture of at least two of its stereoisomers, preferably enantiomers or diastereomers, in any mixing ratio, or a salt, preferably a physiologically acceptable salt thereof, or a corresponding solvate, respectively.

Also preferred is a heterocyclyl-substituted sulfonamide according to the invention according to formula (II), wherein
$R^2$ represents methyl, ethyl, n-propyl, i-propyl, n-butyl, i-butyl and t-butyl; preferably methyl or ethyl;
or
$R^2$ represents hydrogen.

Also preferred is a heterocyclyl-substituted sulfonamide according to the invention according to formula (II), wherein
A represents an unsaturated or aromatic bicyclic heterocyclic ringsystem of 8 to 10 ring members containing 1 to 3 heteroatoms selected from oxygen, nitrogen and sulphur as ring members; optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, or $NH_2$;
preferably
A represents
a radical of general formula III, wherein
X is selected from CH, $CH_2$, CHR, S, O, NR or NH;
Z is selected from C, CH, CR or N;
Ring A is unsaturated or aromatic;
Ring B together with the common ring members from ring A is 5 or 6 membered optionally containing 1 heteroatom selected from oxygen, nitrogen and sulphur as ring member; and is saturated, unsaturated or aromatic;

and Ring A and/or Ring B are optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, or $NH_2$.

Particularly preferred is a heterocyclyl-substituted sulfonamide according to the invention according to either general formula IVA or IVB

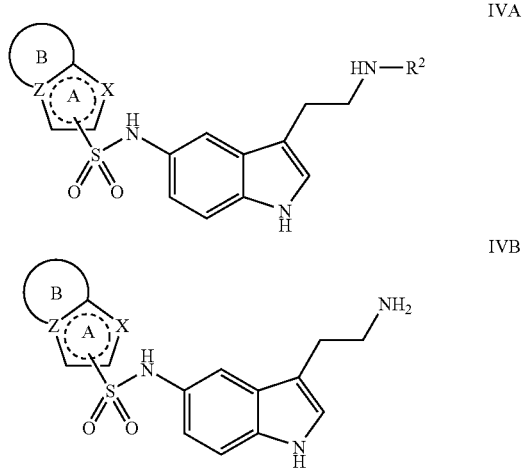

wherein
X is selected from CH, $CH_2$, CHR, S, O, NR or NH;
Z is selected from C, CH, CR or N;
Ring A is unsaturated or aromatic;
Ring B together with the common ring members from ring A is 5 or 6 membered optionally containing 1 heteroatom selected from oxygen, nitrogen and sulphur as ring member; and is saturated, unsaturated or aromatic;
and Ring A and/or Ring B are optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, or $NH_2$;
and
$R^2$ represents methyl, ethyl, n-propyl, i-propyl, n-butyl, i-butyl and t-butyl; preferably methyl or ethyl;
optionally in form of a salt, preferably a physiologically acceptable salt thereof, or a corresponding solvate, respectively.

Particularly preferred is a heterocyclyl-substituted sulfonamide according to the invention according to formula (IVA) or (IVB), wherein the compound is selected from
5-Chloro-3-methyl-benzo[b]thiophene-2-sulfonic acid [3-(2-ethylamino-ethyl)-1H-indol-5-yl]-amide;
5-Chloro-3-methyl-benzo[b]thiophene-2-sulfonic acid [3-(2-methylamino-ethyl)-1H-indol-5-yl]-amide;
6-Chloro-imidazo[2,1-b]thiazole-5-sulfonic acid [3-(2-methylamino-ethyl)-1H-indol-5-yl]-amide; or
6-Chloro-imidazo[2,1-b]thiazole-5-sulfonic acid [3-(2-ethylamino-ethyl)-1H-indol-5-yl]-amide;
or from
5-Chloro-3-methyl-benzo[b]thiophene-2-sulfonic acid [3-(2-amino-ethyl)-1H-indol-5-yl]-amide; or
6-Chloro-imidazo[2,1-b]thiazole-5-sulfonic acid [3-(2-amino-ethyl)-1H-indol-5-yl]-amide;
optionally in form of a salt, preferably a physiologically acceptable salt thereof, or a corresponding solvate, respectively.

A further aspect of this invention provides a production process for the compounds according to the invention as exemplified in the experimental part of the examples (see below).

In a Method A the compounds general formula (I) according to the invention, wherein $R^1$, $R^2$, $R^3$, n and A are as indicated above, can be prepared by reacting a compound with the general formula (V) or one of its suitably protected derivatives

wherein A is as indicated above for the general formula (I) and X is an acceptable leaving group including a halogen atom, particularly chlorine;
with a 5-aminoindol with the general formula (VI), or one of its suitably protected derivatives;

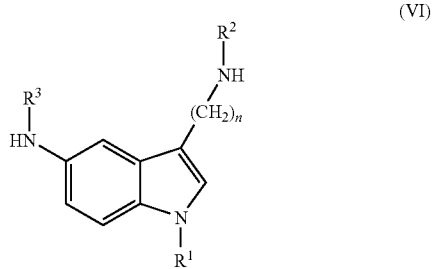

wherein n, $R_1$, $R_2$ and $R_3$ are as indicated above for the general formula (I);
in order to obtain the corresponding sulfonamide and, optionally, eliminating from it the protective groups and/or forming a pharmacologically acceptable salt.

It is preferred that if the compounds according to formulas (V) or (VI) carry a chemical substituent needing protection during the following reaction the substituent is being protected by a protective group, especially those which are well-known to the expert and in the state of the art. Particularly preferred if the hydrogen on the NH-group to which is bound $R^2$ in the compound according to formula (VI) is protected by a protective group, e.g. a Boc-group.

The reaction between the compounds with the general formula (V) and (VI) is carried out in the presence of an organic solvent such as an alkyl ether, particularly diethyl ether, or a cycloalkyl, particularly tetrahydrofurane or dioxane, a halogenated organic hydrocarbon, particularly methylene chloride or chloroform, an alcohol, particularly methanol or ethanol, an aprotic dipolar solvent, particularly acetonitrile, pyridine or dimethylformamide, or any other suitable solvent.

The reaction preferably is carried out in the presence of a suitable inorganic base such as hydroxides and carbonates of alkali metals, or in the presence of an organic base, particularly triethylamine or pyridine.

The most suitable reaction temperatures range from 0° C. to room temperature, and the reaction time is between 5 minutes and 24 hours.

The resulting sulfonamide can be isolated by evaporating the solvent, adding water and eventually adjusting the pH so that it is obtained as a solid that can be isolated by filtration;

or it can be extracted by a solvent immiscible in water such as chloroform and purified by chromatography or recrystallisation from a suitable solvent.

The compounds with the general formula (V) are commercially available or can be prepared according to standard methods or by methods analogous to those described in the literature [E. E. Gilbert, *Synthesis*, 1969, 1, 3] and the compounds with the general formula (VI) can be prepared according to standard methods or by methods analogous to those described in the literature [J. E. Macor, R. Post and K. Ryan, *Synt Comm.*, 1993, 23, 1, 65-72; J. Guillaume, C. Dumont, J. Laurent and N. Nédélec, *Eur. J. Med. Chem.*, 1987, 22, 33-43; M. L. Saccarello, R. Stradi, *Synthesis*, 1979, 727].

Compounds of general formula (I) can be also prepared by one of the following alternative methods:

Method B:

Following the scheme, where a compound of general formula VII is reacted with a compound with the general formula (V) to afford a compound of general formula (VIII).

The reaction between the compounds with general formula (VII) and (V) is carried out in the presence of an organic solvent such as an alkyl ether, particularly diethyl ether, or a cycloalkyl, particularly tetrahydrofurane or dioxane, a halogenated organic hydrocarbon, particularly methylene chloride or chloroform, an alcohol, particularly methanol or ethanol, an aprotic dipolar solvent, particularly acetonitrile, pyridine or dimethylformamide, or any other suitable solvent.

The reaction preferably is carried out in the presence of a suitable inorganic base such as hydroxides and carbonates of alkali metals, or in the presence of an organic base, particularly triethylamine or pyridine.

The most suitable reaction temperatures range from 0° C. to room temperature, and the reaction time is between 5 minutes and 24 hours.

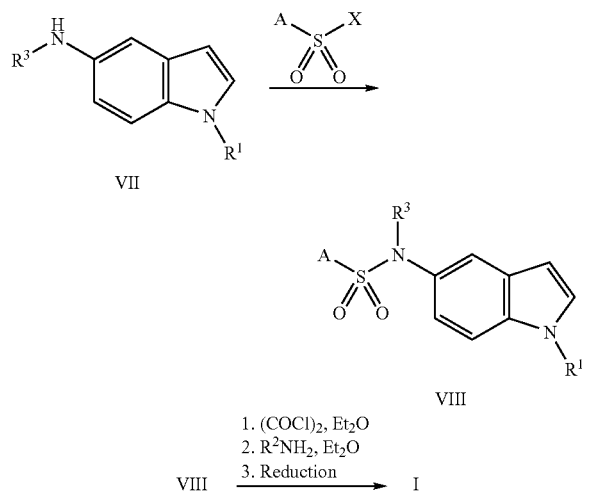

Compounds of general formula (VIII) are transformed into compounds of general formula (I) by a three step process that includes: reaction of compounds of formula (VIII) with oxalyl chloride in a suitable organic solvent, preferably diethyl ether, tetrahydrofuran or dichlormethane. The acid chloride intermediate is then reacted with a suitable amine and the final glyoxamide is reduced, preferably with borane in THF or LiAlH$_4$ as well known in the art (e.g. Macor et al., Synthetic Communications 1993, 23(1), 65-72.

Compounds of general formula (I) with R$^2$=Methyl can be obtained by one of the following two methods C and D:

Method C:

Compounds of general formula (I) with R$^2$=Methyl can be obtained by lithium aluminium hydride reduction of a compound of general formula (IX) according to the scheme below.

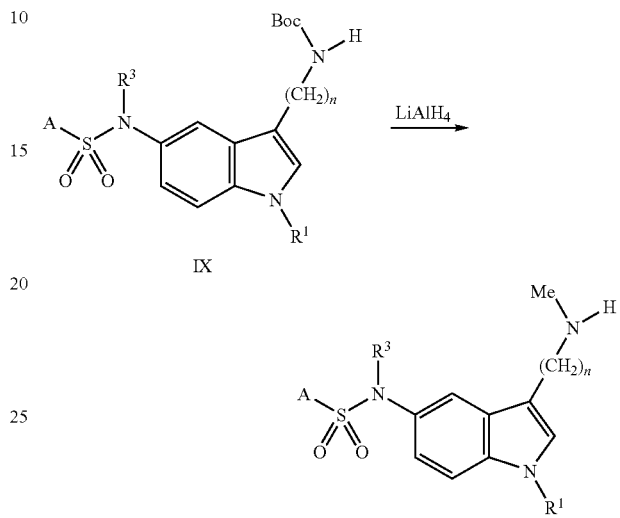

Compounds of general formula (IX) can be obtained by reaction of a compound of general formula (VI) (R$^2$=H and protected with a Boc group) with a compound of general formula (V).

Method D:

Also compounds of general formula (I) with R$^2$=Methyl can be obtained by direct demethylation of a compound of general formula (X) by treatment with a chloroformate according to standard methods or by methods analogous to those described in the literature [J. D. Hobson, J. G. McCluskey, *J. Chem. Soc. C*, 1967, 2015; T. A. Montzka, J. D. Matiskella, R. A. Partyka, *Tetrahedron Lett.*, 1974, 1325; R. A. Olofson, R. C. Schnur, L. Bunes, J. P. Pepe, *Tetrahedron Lett.*, 1977, 1567; R. A. Olofson, J. T. Martz, J. P. Senet, M. Piteau, T. Malfroot, *J. Org. Chem.*, 1984, 49, 2081; D. S. Millan, R. F. Prager, *Tetrahedron Lett.*, 1998, 39, 4387; P. R. Dave, *J. Org. Chem.*, 1996, 61, 5453].

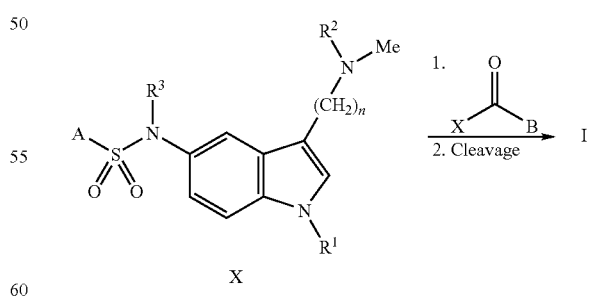

Besides these processes the invention further provides a further aspect in a process for the preparation of salts of compounds of general formula (I), wherein at least one compound of general formula (I) is reacted with an inorganic and/or organic acid, preferably in the presence of a suitable reaction medium. Suitable reaction media are the ones given above. Suitable inorganic acid are for example hydrochloric acid, hydrobromic acid, phosphoric acid, sulphuric acid, nitric acid. Suitable organic acids are e.g. citric acid, maleic acid, fumaric acid, tartaric acid or derivatives thereof, such as p-toluenesulfonic acid, methanesulfonic acid or camphersulfonic acid.

In yet a further aspect the present invention also provides a process for the preparation of salts of compounds of general formula (I), wherein at least one compound of general formula (I) having at least one acidic group is reacted with one or more suitable bases, preferably in the presence of suitable reaction medium. Suitable bases are e.g. hydroxides. Carbonates or alkoxides, which include suitable cations, derived e.g. from alkaline metals, alkaline earth metals or organic cations, e.g. $[NH_nR_{4-n}]^+$, wherein n is 0, 1, 2, 3 or 4 and R represents a branched or linear $C_{1-4}$ alkyl radical.

Solvates, preferably hydrates, of the compounds of general formula (I), or corresponding stereoisomers, or corresponding salts may also be obtained by standard procedures known to those skilled in the art.

If the compounds of general formula (I) are obtained in form of a mixture of stereoisomers, particularly enantiomers or diastereomers, said mixtures may be separated by standard procedures known to those skilled in the art, e.g. chromatographic methods of crystallization with chiral reagents.

The purification and isolation of the compounds of general formula (I) or a corresponding stereoisomer, or a corresponding salt, or corresponding solvate respectively, if required may be carried out by conventional methods known to those skilled in the art, e.g. chromatographic methods or recrystallization.

The compounds of general formula (I), their stereoisomers or the respective salts or solvates are toxicologically acceptable and are therefore suitable as pharmaceutical active substances for the preparation of medicaments.

The present invention therefore also provides for a medicament comprising at least one compound of general formula (I), optionally in form of one of its stereoisomers, preferably enantiomers or diastereomers, its racemate or in form of a mixture of at least two of its stereoisomers, preferably enantiomers or diastereomers, in any mixing ratio, or a physiologically acceptable salt thereof, or a solvate, respectively, and optionally one or more pharmaceutically acceptable adjuvants.

Furthermore, the present invention also provides for a pharmaceutical composition comprising at least one compound of general formula (I), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and optionally one or more pharmaceutically acceptable adjuvants, which is not yet formulated into a medicament.

Preferably the medicament is suitable for the regulation off or regulation of appetite, for maintenance, increase or reduction of body weight, for prophylaxis and/or treatment of disorders related to food ingestion, preferably for prophylaxis and/or treatment of obesity, anorexia, cachexia, bulimia, diabetes, preferably type II diabetes (non-insulin-dependent diabetes mellitus), or for prophylaxis and/or treatment of gastrointestinal tract disorders, preferably of the irritable bowel syndrome, for prophylaxis and/or treatment of Metabolic Syndrome, Peripheral Nervous System Disorders, Central Nervous System Disorders, arthritis, epilepsy, anxiety, panic, depression, cognitive disorders, memory disorders, cardiovascular diseases, senile dementia processes, such as Alzheimer's, Parkinson's and/or Huntington's Disease, schizophrenia, psychosis, infantile hyperkinesia (ADHD, attention deficit/hyperactivity disorder), pain, hypertensive syndrome, inflammatory diseases, immunologic diseases or for improvement of cognition.

The present invention also provides for the use of at least one compound of general formula (I), optionally in form of one of its stereoisomers, preferably enantiomers or diastereomers, its racemate or in form of a mixture of at least two of its stereoisomers, preferably enantiomers or diastereomers, in any mixing ratio, or a physiologically acceptable salt thereof, or a solvate, respectively, for the manufacture of a medicament for the prophylaxis and/or treatment of disorders related to food ingestion, preferably for prophylaxis and/or treatment of obesity, anorexia, cachexia, bulimia, diabetes, preferably type II diabetes (non-insulin-dependent diabetes mellitus), or for prophylaxis and/or treatment of gastrointestinal tract disorders, preferably of the irritable bowel syndrome, for prophylaxis and/or treatment of Metabolic Syndrome, Peripheral Nervous System Disorders, Central Nervous System Disorders, arthritis, epilepsy, anxiety, panic, depression, cognitive disorders, memory disorders, cardiovascular diseases, senile dementia processes, such as Alzheimer's, Parkinson's and/or Huntington's Disease, schizophrenia, psychosis, infantile hyperkinesia (ADHD, attention deficit/hyperactivity disorder), pain, hypertensive syndrome, inflammatory diseases, immunologic diseases or for improvement of cognition The medicament may be in any form suitable for the application to humans and/or animals, preferably mammals, and can be produced by standard procedures known to those skilled in the art. The composition of the medicament may vary depending on the route of administration.

The medicament of the present invention may e.g. be administered parentally in combination with conventional injectable liquid carriers, such as water or suitable alcohols. Conventional pharmaceutical adjuvants for injection, such as stabilizing agents, solubilizing agents, and buffers, may be included in such injectable compositions. These medicaments may preferably be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered form suitable for reconstitution with water or other suitable liquid medium before use, for immediate or controlled release.

The liquid oral forms for administration may also contain certain additives such as sweeteners, flavoring, preservatives, and emulsifying agents. Non-aqueous liquid compositions for oral administration may also be formulated, containing e.g. edible oils. Such liquid compositions may be conveniently encapsulated in e.g., gelatin capsules in a unit dosage amount.

The compositions of the present invention may also be administered topically or via a suppository.

The above mentioned compositions include preferably 1 to 60% by weight of one or more of the compound of general formula (I), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and 40 to 99% by weight of the appropriate pharmaceutical vehicle(s).

The daily dosage for humans and animals may vary depending on factors that have their basis in the respective species or other factors, such as age, weight or degree of illness and so forth. The daily dosage for mammals including humans usually ranges from 1 milligram to 2000 milligram, preferably 1 to 1500 mg, more preferably 1 to 1000 mg of substance to be administered during one or several intakes.

The following examples are provided to illustrate the claimed invention and are not meant to limit it in any way.

EXAMPLES

The examples were prepared by the following general method:

A compound of general formula (V) or one of its suitably protected derivatives

(V)

wherein A is as indicated above for the general formula (I) and X is an acceptable leaving group including a halogen atom, particularly chlorine; is reacted with a 5-aminoindol with the general formula (VI), or one of its suitably protected derivatives;

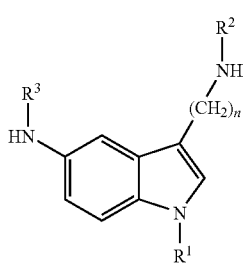

(VI)

wherein n, $R_1$, $R_2$ and $R_3$ are as indicated above for the general formula (I); in order to obtain the corresponding sulfonamide and, optionally, eliminating from it the protective groups and/or forming a pharmacologically acceptable salt.

Example 2

Preparation of 5-Chloro-3-methyl-benzo[b]thiophene-2-sulfonic acid [3-(2-methylamino-ethyl)-1H-indol-5-yl]-amide

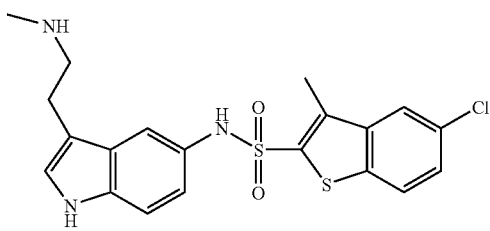

5-Chloro-3-methyl-benzo[b]thiophene-2-sulfonic acid [3-(2-methylamino-ethyl)-1H-indol-5-yl]-amide The compound was prepared according to the following scheme:

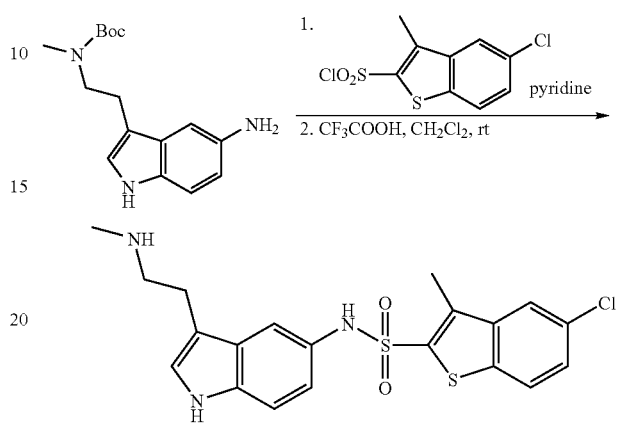

To a solution of 2.89 g (10 mMol) of tert-butyl 2-(5-amino-1H-indol-3-yl)ethyl(methyl) carbamate in 100 ml of pyridine is added dropwise at room temperature a solution of 2.81 g (10 mMol) of 5-chloro-3-methyl-benzo[b]thiophene-2-sulfonyl chloride in 20 ml of pyridine. The reaction mixture is stirred at room temperature for 20 hours. It is then evaporated to dryness, slightly alkalinised with diluted ammonia and dissolved in ethyl acetate. The organic phase is washed with water and a saturated solution of sodium bicarbonate, it is separated and dried with anhydrous sodium sulphate. The organic solution is evaporated to dryness and the resulting Boc-protected sulfonamide is treated with a 5% solution of trifluoroacetic acid in dichloromethane to yield 5-Chloro-3-methyl-benzo[b]thiophene-2-sulfonic acid [3-(2-methylamino-ethyl)-1H-indol-5-yl]-amide.

The other examples 1 and 3 to 6 are prepared in an analogue manner.

Example 1

5-Chloro-3-methyl-benzo[b]thiophene-2-sulfonic acid [3-(2-ethylamino-ethyl)-1H-indol-5-yl]-amide

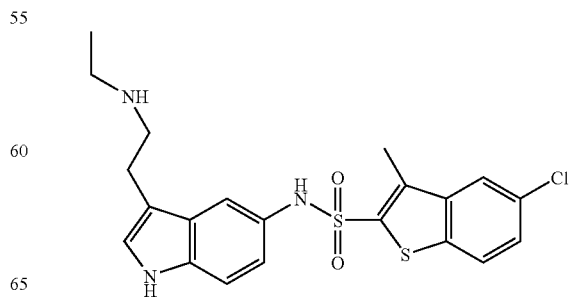

5-Chloro-3-methyl-benzo[b]thiophene-2-sulfonic acid [3-(2-ethylamino-ethyl)-1H-indol-5-yl]-amide Example 3

6-Chloro-imidazo[2,1-b]thiazole-5-sulfonic acid [3-(2-methylamino-ethyl)-1H-indol-5-yl]-amide

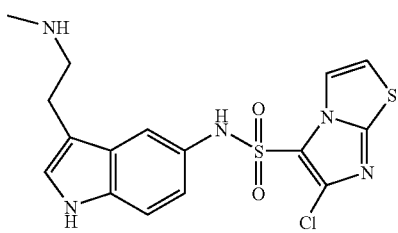

6-Chloro-imidazo[2,1-b]thiazole-5-sulfonic acid [3-(2-methylamino-ethyl)-1H-indol-5-yl]-amide Example 4

6-Chloro-imidazo[2,1-b]thiazole-5-sulfonic acid [3-(2-ethylamino-ethyl)-1H-indol-5-yl]-amide

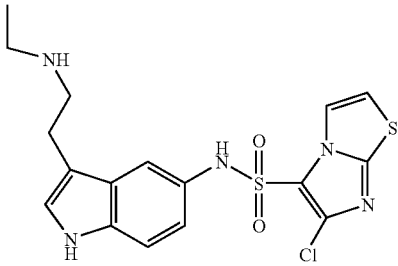

6-Chloro-imidazo[2,1-b]thiazole-5-sulfonic acid [3-(2-ethylamino-ethyl)-1H-indol-5-yl]-amide Example 5

5-Chloro-3-methyl-benzo[b]thiophene-2-sulfonic acid [3-(2-amino-ethyl)-1H-indol-5-yl]-amide

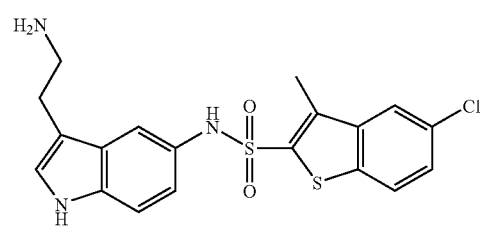

5-Chloro-3-methyl-benzo[b]thiophene-2-sulfonic acid [3-(2-amino-ethyl)-1H-indol-5-yl]-amide Example 6

6-Chloro-imidazo[2,1-b]thiazole-5-sulfonic acid [3-(2-amino-ethyl)-1H-indol-5-yl]-amide

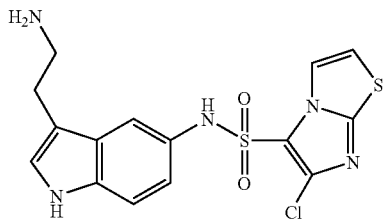

6-Chloro-imidazo[2,1-b]thiazole-5-sulfonic acid [3-(2-amino-ethyl)-1H-indol-5-yl]-amide The examples are also listed in the following table:

| Ex | $R_1$ | $R_2$ | n | $R_3$ | A | Salt | $^1$H-NMR (300 MHz), δ (solvent) |
|---|---|---|---|---|---|---|---|
| 1 | H | $C_2H_5$ | 2 | H | 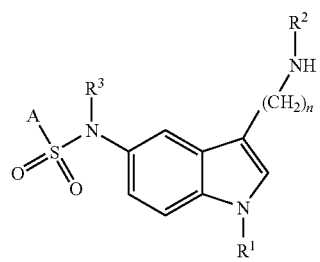 | | 0.85 (t, 3H, J=6.9 Hz); 2.30 (s, 3H); 2.42-2.48 (m, 2H); 2.63 (bb, 4H); 6.77 (d, 1H, J=8.7 Hz); 7.07 (s, 1H); 7.14-7.16 (m, 2H); 7.48 (d, 1H, J=8.7 Hz); 7.89 (s, 1H); 7.97 (d, 1H, J= 8.7 Hz); 10.76 (s, 1H) (DMSO-d6) |

-continued

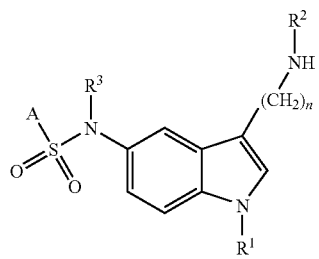

| Ex | R₁ | R₂ | n | R₃ | A | Salt | $^1$H-NMR (300 MHz), δ (solvent) |
|----|----|----|---|----|---|------|-----------------------------------|
| 2 | H | CH$_3$ | 2 | H | ![benzothiophene with Cl, CH3, CH3] | | 2.32 (s, 3H); 2.38 (s, 3H); 2.81 (bb, 4H); 6.75 (d, 1H, J=8.7 Hz); 7.16 (s, 1H); 7.19 (d, 1H, J=8.7 Hz); 7.26 (s, 1H); 7.50 (dd, 1H, J=8.7, 1.8 Hz); 7.92 (d, 1H, J=1.5 Hz); 8.00 (d, 1H, J=8.7 Hz); 10.92 (s, 1H) (DMSO-d6) |
| 3 | H | CH$_3$ | 2 | H | ![imidazothiazole with Cl, Me] | | 2.36 (s, 3H); 2.72 (bb, 4H); 6.69 (dd, 1H, J=8.7, 2.1 Hz); 7.05 (d, 1H, J=2.4 Hz); 7.10 (d, 1H, J=2.1 Hz); 7.11 (d, 1H, J=8.4 Hz); 7.46 (d, 1H, J=4.5 Hz); 7.84 (d, 1H, J=4.5 Hz); 10.67 (bb, 1H) (DMSO-d6) |
| 4 | H | C$_2$H$_5$ | 2 | H | ![imidazothiazole with Cl, Me] | | 1.17 (t, 3H, J=7.2 Hz); 2.92-3.05 (m, 6 H); 6.69 (dd, 1H, J= 8.7, 2.1 Hz); 7.19-7.27 (m, 3H); 7.54 (d, 1H, J=4.5 Hz); 7.83 (d, 1H, J=4.5 Hz); 10.99 (bb, 1H) (DMSO-d6) |
| 5 | H | H | 2 | H | ![benzothiophene with Cl, CH3, CH3] | | 2.34 (s, 3H); 2.61-2.74 (m, 4H); 6.73 (dd, 1H, J=8.1, 2.1 Hz); 7.04 (d, 1H, J=2.4 Hz); 7.09 (d, 1H, J=8.7 Hz); 7.17 (d, 1H, J=2.1 Hz); 7.46 (dd, 1H, J=8.4, 1.8 Hz); 7.87 (d, 1H, J=2.1 Hz); 7.95 (d, 1H, J=8.7 Hz); 10.68 (bb, 1H) (DMSO-d6) |
| 6 | H | H | 2 | H | ![imidazothiazole with Cl, Me] | | 2.71-2.83 (m, 4H); 6.63 (dd, 1H, J=8.7, 2.1 Hz); 7.00 (d, 1H, J=2.1 Hz); 7.03 (d, 1H, J=8.7 Hz); 7.08 (d, 1H, J=1.8 Hz); 7.39 (d, 1H, J=4.5 Hz); 7.86 (d, 1H, J=4.5 Hz); 10.54 (bb, 1H) (DMSO-d6) |

Biological Assays

Binding with Serotonin Receptor 5HT$_6$

Cell membranes of HEK-293 cells expressing the 5HT$_6$ human recombinant receptor were supplied by Receptor Biology. In said membranes the receptor concentration is 2.18 pmol/mg protein and the protein concentration is 9.17 mg/ml. The experimental protocol follows the method of B. L. Roth et al. [B. L. Roth, S. C. Craigo, M. S. Choudhary, A. Uluer, F. J. Monsma, Y. Shen, H. Y. Meltzer, D. R. Sibley: Binding of Typical and Atypical Antipsychotic Agents to 5-Hydroxytryptamine-6 and Hydroxytryptamine-7 Receptors. *The Journal of Pharmacology and Experimental Therapeutics*, 1994, 268, 1403] with slight changes. The commercial membrane is diluted (1:40 dilution) with the binding buffer: 50 mM Tris-HCl, 10 mM MgCl$_2$, 0.5 mM EDTA (pH 7.4). The radioligand used is [$^3$H]-LSD at a concentration of 2.7 nM with a final volume of 200 μl. incubation is initiated by adding 100 μl of membrane suspension, (≈22.9 μg membrane protein), and is prolonged for 60 minutes at a temperature of 37° C. The incubation is ended by fast filtration in a Brandel Cell Harvester through fiber glass filters made by Schleicher & Schuell GF 3362 pretreated with a solution of polyethylenimine at 0.5%. The filters are washed three times with three milliliters of buffer Tris-HCl 50 mM pH 7.4. The filters are transferred to flasks and 5 ml of Ecoscint H liquid scintillation cocktail are added to each flask. The flasks are allowed to reach equilibrium for several hours before counting with a Wallac Winspectral 1414 scintillation counter. Non-specific binding is determined in the presence of 100 μM of serotonin. Tests were made in triplicate. The inhibition constants (K$_i$, nM) were calculated by non-linear regression analysis using the program EBDA/LIGAND [Munson and Rodbard, *Analytical Biochemistry*, 1980, 107, 220]. The following table shows results indicative of binding for some of the compounds object of the present invention.

TABLE

| Example | Binding % Inhibition 100 nM | Binding % Inhibition 10 nM | $K_i$ (nM) |
| --- | --- | --- | --- |
| 1 | 91.4 | 82.7 | 0.67 |
| 2 | 80.3 | 62.5 | 2.0 |
| 3 | 71.8 | 47.3 | 4.7* |
|   |      |      | 3.2 ± 1.6* |
| 4 | 81.7 | 61.8 | 6.4 ± 1.0 |
| 5 | 85.0 | 63.5 | 11.7 |
| 6 | 92.3 | 75.7 | 3.6 ± 1.4 |

*Two different experiments/calculations.

The daily doses in human medicine are between 1 milligram and 500 milligrams of product, which can be given in one or more administrations. The compositions are prepared in forms compatible with the administration means used, such as sugar-coated pills, tablets, capsules, suppositories, solutions or suspensions. These compositions are prepared by known methods and comprise between 1 and 60% by weight of the active principle (compound with the general formula I) and 40 to 99% by weight of a suitable pharmaceutical vehicle compatible with the active principle and the physical form of the composition used. By way of example, the formula of a tablet containing a product of the invention is shown.

Example of formula per tablet:

| | |
| --- | --- |
| Example 3 | 5 mg |
| Lactose | 60 mg |
| Crystalline cellulose | 25 mg |
| K 90 Povidone | 5 mg |
| Pregelatinised starch | 3 mg |
| Colloidal silicon dioxide | 1 mg |
| Magnesium stearate | 1 mg |
| Total weight per tablet | 100 mg |

The invention claimed is:

1. A heterocyclyl-substituted sulfonamide compound, or a salt thereof, according to general formula (I)

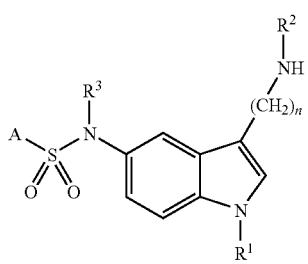

wherein

A represents a substituted or unsubstituted mono or bicyclic heterocyclic ring system with 1 to 3 heteroatoms selected from oxygen, nitrogen and sulphur;

$R^1$ represents hydrogen, $C_1$-$C_4$ alkyl or a benzyl radical;

$R^2$ represents $C_2$-$C_4$ alkyl;

$R^3$ represents hydrogen or $C_1$-$C_4$ alkyl; and n represents 0, 1, 2, 3 or 4.

2. A heterocyclyl-substituted sulfonamide compound, or a salt thereof, according to claim 1, wherein
A represents
a substituted or unsubstituted monocyclic heterocyclic ring system of 5 to 6 ring members containing 1 to 3 heteroatoms selected from oxygen, nitrogen and sulphur as ring members; or
an optionally at least mono-substituted bicyclic heterocyclic ring system of 8 to 10 ring members containing 1 to 3 heteroatoms selected from oxygen, nitrogen and sulphur as ring members.

3. A heterocyclyl-substituted sulfonamide compound, or a salt thereof, according to claim 2, wherein A represents
a) an unsaturated or aromatic monocyclic heterocyclic ring system of 5 to 6 ring members containing 1 to 3 heteroatoms selected from oxygen, nitrogen and sulphur as ring members, optionally substituted by 1 or 2 radicals R or R' selected from:
halogen, $C_1$-$C_4$ alkyl, O—$C_1$-$C_4$ alkyl, CN, $NO_2$, $CF_3$, $CHF_2$, $OCF_3$, OH, SH, and $NH_2$;
phenyl, optionally at least monosubstituted by halogen, $C_1$-$C_4$ alkyl, O—$C_1$-$C_4$ alkyl, OH, SH, or $NH_2$; and
a monocyclic heterocyclic ring system with 5 or 6 ring members containing 1 or 2 atoms of oxygen, nitrogen or sulphur as ring member, at least monosubstituted by halogen, $C_1$-$C_4$ alkyl, O—$C_1$-$C_4$ alkyl, OH, SH, or $NH_2$; or
b) an unsaturated or aromatic bicyclic heterocyclic ring system of 8 to 10 ring members containing 1 to 3 heteroatoms selected from oxygen, nitrogen and sulphur as ring members; optionally substituted by 1 or 2 radicals R or R' selected from:
halogen, $C_1$-$C_4$ alkyl, O—$C_1$-$C_4$ alkyl, CN, $NO_2$, $CF_3$, $CHF_2$, $OCF_3$, OH, SH, and $NH_2$;
phenyl, optionally at least monosubstituted by halogen, $C_1$-$C_4$ alkyl, O—$C_1$-$C_4$ alkyl, OH, SH, or $NH_2$; and
a monocyclic heterocyclic ring system with 5 or 6 ring members containing 1 or 2 atoms of oxygen, nitrogen or sulphur as ring member, at least monosubstituted by halogen, $C_1$-$C_4$ alkyl, O—$C_1$-$C_4$ alkyl, OH, SH, or $NH_2$.

4. A heterocyclyl-substituted sulfonamide compound, or a salt thereof, according to claim 3, wherein A represents
a) an unsaturated or aromatic monocyclic heterocyclic ring system of 5 to 6 ring members containing 1 to 3 heteroatoms selected from oxygen, nitrogen and sulphur as ring members, optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, and $NH_2$; or
b) an unsaturated or aromatic bicyclic heterocyclic ring system of 8 to 10 ring members containing 1 to 3 heteroatoms selected from oxygen, nitrogen and sulphur as ring members, optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, and $NH_2$.

5. A heterocyclyl-substituted sulfonamide compound, or a salt thereof, according to claim 1, wherein $R^1$ represents hydrogen, $CH_3$, $C_2H_5$, $C_3H_7$ or $C_4H_9$.

6. A heterocyclyl-substituted sulfonamide compound, or a salt thereof, according to claim 5, wherein $R^1$ represents hydrogen, methyl or ethyl.

7. A heterocyclyl-substituted sulfonamide compound, or a salt thereof, according to claim 6, wherein $R^1$ represents hydrogen.

8. A heterocyclyl-substituted sulfonamide compound, or a salt thereof, according to claim 1, wherein $R^2$ represents $C_2H_5$, $C_3H_7$ or $C_4H_9$.

9. A heterocyclyl-substituted sulfonamide compound, or a salt thereof, according to claim 8, wherein $R^2$ represents ethyl.

10. A heterocyclyl-substituted sulfonamide compound, or a salt thereof, according to claim 1 wherein $R^3$ represents hydrogen, $CH_3$, $C_2H_5$, $C_3H_7$ or $C_4H_9$.

11. A heterocyclyl-substituted sulfonamide compound, or a salt thereof, according to claim 10, wherein $R^3$ represents hydrogen, methyl or ethyl.

12. A heterocyclyl-substituted sulfonamide compound, or a salt thereof, according to claim 11, wherein $R^3$ represents hydrogen.

13. A heterocyclyl-substituted sulfonamide compound, or a salt thereof, according to claim 1, wherein n represents 0, 1 or 2.

14. A heterocyclyl-substituted sulfonamide compound, or a salt thereof, according to claim 13, wherein n represents 2.

15. A heterocyclyl-substituted sulfonamide compound, or a salt thereof, according to claim 1 wherein the compound of formula I is a compound of formula II,

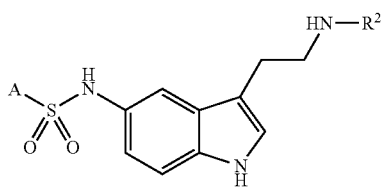

II wherein

A represents an unsaturated or aromatic monocyclic heterocyclic ring system of 5 to 6 ring members containing 1 to 3 heteroatoms selected from oxygen, nitrogen and sulphur as ring members, optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, and $NH_2$; or an unsaturated or aromatic bicyclic heterocyclic ring system of 8 to 10 ring members containing 1 to 3 heteroatoms selected from oxygen, nitrogen and sulphur as ring members, optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, and $NH_2$; and $R^2$ represents $C_2H_5$, $C_3H_7$ or $C_4H_9$.

16. A heterocyclyl-substituted sulfonamide compound, or a salt thereof, according to claim 15, wherein $R^2$ represents ethyl, n-propyl, i-propyl, n-butyl, i-butyl and t-butyl.

17. A heterocyclyl-substituted sulfonamide compound, or a salt thereof, according to claim 15, wherein $R^2$ represents ethyl.

18. A heterocyclyl-substituted sulfonamide compound, or a salt thereof, according to claim 15, wherein A represents an unsaturated or aromatic bicyclic heterocyclic ring system of 8 to 10 ring members containing 1 to 3 heteroatoms selected from oxygen, nitrogen and sulphur as ring members, optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, and $NH_2$.

19. A heterocyclyl-substituted sulfonamide compound, or a salt thereof, according to claim 18 wherein A represents a radical of general formula III

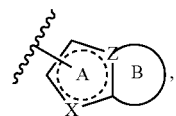

III wherein

X is selected from CH, $CH_2$, CHR, S, O, NR and NH;

Z is selected from C, CH, CR and N;

Ring A is unsaturated or aromatic;

Ring B together with the common ring members from ring A is 5 or 6 membered optionally containing 1 heteroatom selected from oxygen, nitrogen and sulphur as ring member; and is saturated, unsaturated or aromatic; and Ring A and Ring B are each optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, and $NH_2$.

20. A heterocyclyl-substituted sulfonamide compound, or a salt thereof, according to claim 15, wherein the compound is a compound according to either general formula IVA or IVB

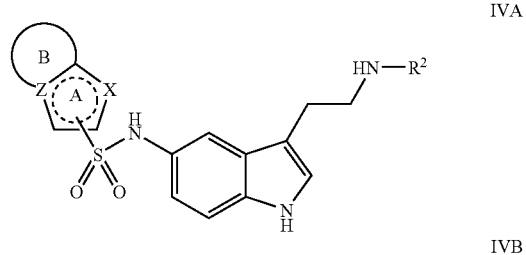

IVA

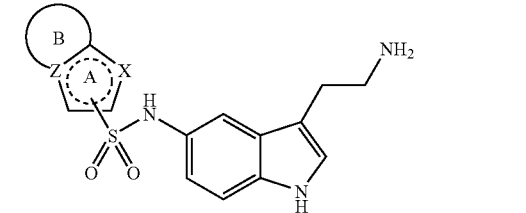

IVB wherein

X is selected from CH, $CH_2$, CHR, S, O, NR and NH;

Z is selected from C, CH, CR and N;

Ring A is unsaturated or aromatic;

Ring B together with the common ring members from ring A is 5 or 6 membered optionally containing 1 heteroatom selected from oxygen, nitrogen and sulphur as ring member; and is saturated, unsaturated or aromatic; and Ring A and Ring B are each optionally substituted by 1 or 2 radicals R or R' selected from halogen, $C_1$-$C_4$ alkyl, O—$C_1$-$C_4$ alkyl, $CF_3$, $CHF_2$, $OCF_3$, OH, SH, or $NH_2$; and $R^2$ represents ethyl, n-propyl, i-propyl, n-butyl, i-butyl and t-butyl.

21. A heterocyclyl-substituted sulfonamide compound, or a salt thereof, according to claim 20, wherein $R^2$ represents ethyl.

22. A heterocyclyl-substituted sulfonamide compound, or a salt thereof, according to claim 20, wherein the compound is selected from 5-Chloro-3-methyl-benzo[b]thiophene-2-sulfonic acid [3-(2-ethylamino-ethyl)-1H-indol-5-yl]-amide; and 6-Chloro-imidazo[2,1-b]thiazole-5-sulfonic acid[3-(2-ethylamino-ethyl)-1H-indol-5-yl]-amide.

23. A composition comprising at least one compound, or a salt thereof, according to claim 1 and optionally one or more pharmacologically acceptable excipients.

* * * * *